United States Patent [19]

Gallay et al.

[11] 4,197,307
[45] Apr. 8, 1980

[54] 2-ALKYLTHIO-, 2-ALKYLSULPHINYL- AND 2-ALKYLSULFONYL-6-PHENYLBEN-ZIMIDAZOLES AS ANTHELMINTIC AGENTS

[75] Inventors: Jean-Jacques Gallay, Magden; Manfred Kühne, Pfeffingen; Alfred Meyer, Basel; Oswald Rechsteiner, Binningen; Max Schellenbaum, Muttenz, all of Switzerland

[73] Assignee: Ciba-Geigy Corporation, Ardsley, N.Y.

[21] Appl. No.: 894,973

[22] Filed: Apr. 10, 1978

[30] Foreign Application Priority Data

Apr. 12, 1977 [LU] Luxembourg .................. 77120
Mar. 15, 1978 [LU] Luxembourg .................. 79232

[51] Int. Cl.² .................. A61K 31/415; C07D 235/28
[52] U.S. Cl. .................. 424/273 B; 548/305; 548/328; 548/329
[58] Field of Search .................. 548/329, 328; 424/273 R, 273 B

[56] References Cited

U.S. PATENT DOCUMENTS

| | | | |
|---|---|---|---|
| 2,666,764 | 1/1954 | Lanzilotti et al. | 548/329 |
| 3,480,643 | 11/1969 | Lutz et al. | 548/329 |
| 3,506,767 | 4/1970 | Frick et al. | 548/329 |
| 3,555,040 | 1/1971 | Frick et al. | 548/329 |
| 3,669,981 | 6/1972 | Pera et al. | 548/329 |
| 3,933,841 | 1/1976 | Brenneisen | 548/329 |

FOREIGN PATENT DOCUMENTS 1509192  12/1967  France ................... 548/329

Primary Examiner—Natalie Trousof
Attorney, Agent, or Firm—Frederick H. Rabin

[57] ABSTRACT

Benzimidazole derivatives of the formula

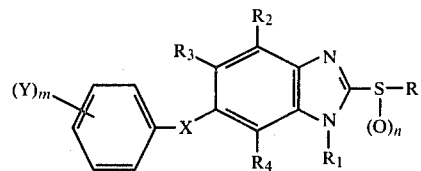

in which
R is an alkyl group having 1 to 6 carbon atoms, an alkenyl group having 3 to 5 carbon atoms, an alkynyl group having 3 to 5 carbon atoms or a benzyl group, which is unsubstituted or monosubstituted to disubstituted by a methyl group, halogen or a nitro group;
$R_1$ is hydrogen, an alkanoyl group having 1 to 4 carbon atoms, an alkoxycarbonyl group having 1 to 4 carbon atoms, a N,N-dialkylcarbamoyl group or N,N-dialkylthiocarbamoyl group, each having 1 to 4 carbon atoms in the alkyl groups, an alkylsulphonyl group having 1 to 4 carbon atoms, a benzoyl group, a phenylsulphonyl group, a 4-methylphenylsulphonyl group or the radical,

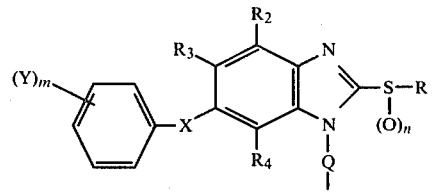

in which
Q is a carbonyl group, a thiocarbonyl group or an oxalyl group;
$R_2$ is hydrogen, halogen or a methyl group;
$R_3$ is hydrogen, halogen, a methyl group or an alkoxy group having 1 to 4 carbon atoms;
$R_4$ is hydrogen, halogen or a methyl group; X is oxygen or sulphur;
Y is halogen, an alkyl group having 1 to 4 carbon atoms, an alkoxy group having 1 to 4 carbon atoms, a methylthio group, a methylsulphinyl group, a methylsulphonyl group, a trifluoromethyl group, a nitro group, a hydroxyl group, a cyano group or an alkanoyl group having 1 to 4 carbon atoms in the alkyl moiety m is 0, 1, 2 or 3; and
n is 0, 1 or 2.

Included are, if $R_1$ is not hydrogen, the tautomeric compounds of the formula I. The compounds are effective for combating helminths in domestic and useful animals.

23 Claims, No Drawings

2-ALKYLTHIO-, 2-ALKYLSULPHINYL- AND 2-ALKYLSULFONYL-6-PHENYLBENZIMIDAZOLES AS ANTHELMINTIC AGENTS

DETAILED DISCLOSURE

The present invention relates to novel benzimidazole derivatives having an anthelmintic activity, processes for the preparation of these compounds, agents containing these compounds as the active component and their use for combating helminths, especially trematodes, in domestic and useful animals.

The compounds according to the invention are of the general formula I

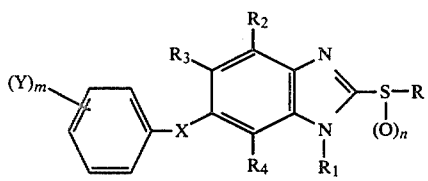

in which

R is an alkyl group having 1 to 6 carbon atoms, an alkenyl group having 3 to 5 carbon atoms, an alkynyl group having 3 to 5 carbon atoms or a benzyl group, which is unsubstituted or monosubstituted to disubstituted by a methyl group, halogen or a nitro group;

$R_1$ is hydrogen, an alkanoyl group having 1 to 4 carbon atoms, an alkoxycarbonyl group having 1 to 4 carbon atoms, a N,N-dialkylcarbamoyl group or N,N-dialkylthiocarbamoyl group, each having 1 to 4 carbon atoms in the alkyl groups, an alkylsulphonyl group having 1 to 4 carbon atoms, a benzoyl group, a phenylsulphonyl group, a 4-methylphenylsulphonyl group or the radical

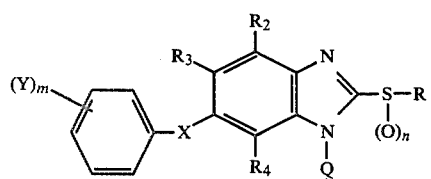

in which

Q is a carbonyl group, a thiocarbonyl group or an oxalyl group;

$R_2$ is hydrogen, halogen or a methyl group;

$R_3$ is hydrogen, halogen, a methyl group or an alkoxy group having 1 to 4 carbon atoms;

$R_4$ is hydrogen, halogen or a methyl group;

X is oxygen or sulphur;

Y is halogen, an alkyl group having 1 to 4 carbon atoms, an alkoxy group having 1 to 4 carbon atoms, a methylthio group, a methylsulphinyl group, a methylsulphonyl group, a trifluoromethyl group, a nitro group, a hydroxyl group, a cyano group or an alkanoyl group having 1 to 4 carbon atoms in the alkyl moiety; m is 0, 1, 2 or 3; and n is 0, 1 or 2.

Included are, if $R_1$ is not hydrogen, the tautomeric compounds of the formula I.

Halogen, as $R_2$, $R_3$ and $R_4$ in formula I and as Y in formula IV, is to be understood as meaning, preferably, chlorine or bromine.

In the present description, "helminths" are to be understood as meaning parasitic nematodes, cestodes and trematodes in the gastrointestinal tract or in other organs.

Amongst the endoparasites occurring in warm-blooded animals, the helminths in particular cause great damage. Thus, animals infested by these parasites display not only a retarded growth and a distinctly reduced performance but, in some cases, such severe damage that the diseased animals die. In order to prevent or at least lessen losses of returns from this type in animal husbandry, which can assume considerable proportions if cases of infestation with worms in the animal herds are of an epidemic nature, efforts are continually being made to provide agents for combating helminths, including their development stages.

It is true that a number of substances having an anthelmintic activity are known, but these active ingredients are not able to meet the demands made on them in the desired manner since, for example, they do not exhibit an adequate activity in every case when administered in tolerated doses or, when administered in a therapeutically effective dosage, can cause undesired side effects, such as intoxications.

Thus, for example, benzimidazole derivatives are mentioned in British patent specification No. 1,344,548 and in French patent specification No. 1,476,558 for use in various fields, including, in the latter specification, in a general form, the possibility of use against helminths.

It is now proposed to employ the benzimidazole derivatives, according to the invention, of the formula I for combating helminths.

The benzimidazole derivatives of the formula I are distinguished by superior anthelmintic activity, especially against trematodes, and in particular their action against Fasciolidae (for example *Fasciola hepatica*) is to be singled out.

Amongst these derivatives, the compounds which fall under the following restricted formula II are to be regarded as preferred, in respect of their activity:

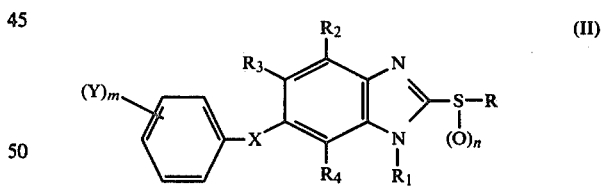

in which

R is an alkyl group having 1 to 6 carbon atoms, an alkenyl group having 3 to 5 carbon atoms, an alkynyl group having 3 to 5 carbon atoms or a benzyl group which is unsubstituted or monosubstituted to disubstituted by a methyl group, halogen or a nitro group;

$R_1$ is hydrogen, an alkanoyl group having 1 to 4 carbon atoms, an alkoxycarbonyl group having 1 to 4 carbon atoms or a benzoyl group;

$R_2$ is hydrogen, chlorine or a methyl group;

$R_3$ is hydrogen, chlorine, a methyl group or a methoxy group;

$R_4$ is hydrogen, chlorine or a methyl group;

X is oxygen or sulphur;

Y is halogen, a methyl group, a methoxy group, a methylthio group, a methylsulphinyl group, a methylsulphonyl group, an acetyl group, a hydroxyl group, a nitro group or a cyano group; m is 0, 1, 2 or 3; and n is 0, 1 or 2.

Included are, if $R_1$ is not hydrogen, the tautomeric compounds of the formula II.

Furthermore, compounds of the following restricted formula III are characterised by high activity:

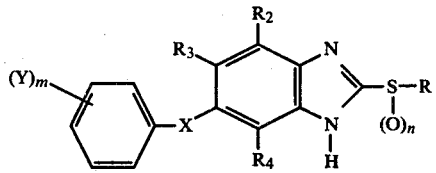

in which

R is an alkyl group having 1 to 6 carbon atoms, an alkenyl group having 3 to 5 carbon atoms, an alkynyl group having 3 to 5 carbon atoms or a benzyl group which is unsubstituted or monosubstituted to disubstituted by a methyl group, halogen or a nitro group;

$R_2$ is hydrogen, chlorine or a methyl group;

$R_3$ is hydrogen, chlorine, a methyl group or a methoxy group;

$R_4$ is hydrogen, chlorine or a methyl group; X is group or sulphur; and

Y is halogen, a methyl group, a methoxy group, a methylthio group, a methylsulphinyl group, a methylsulphonyl group, an acetyl group, a hydroxyl group, a nitro group or a cyano group;

m is 0, 1, 2 or 3; and n is 0, 1 or 2.

Moreover, compounds of the following restricted formula IV are distinguished by an advantageous therapeutic activity:

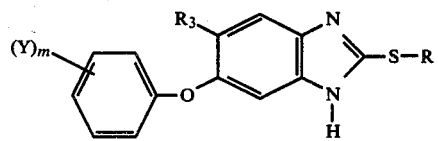

in which

R is an alkyl group having 1 to 6 carbon atoms, $R_3$ is hydrogen, chlorine or a methyl group; and Y is halogen or a methyl group, with the proviso that the 2-position of the phenyl radical bonded via an oxygen atom must always be occupied by a substituent as defined for Y and the 6-position of this phenyl radical must always be unoccupied; and m is 1 or 2.

The starting compounds used to prepare the compounds of the formulae I-IV can be prepared by the following processes:

a)

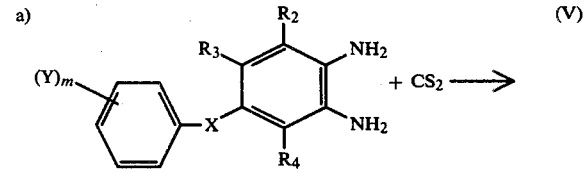

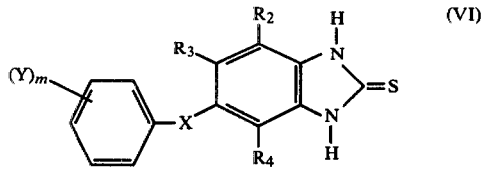

in which formulae $R_2$, $R_3$, $R_4$, X, Y and m are as defined under formula I.

The reaction takes place at temperatures of 10° to 150° C., preferably 30° to 100° C., in water or organic solvents, in the presence of a base.

Examples or organic solvents are alcohols, such as methanol, ethanol of the propyl alcohols, or hydrocarbons, such as benzene or toluene, or chlorinated hydrocarbons, such as chlorobenzene or methylene chloride. Bases are to be understood as meaning, for example, an alkali, tertiary amines or organic bases, such as pyridine.

b) 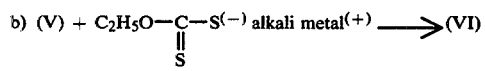

The reaction takes place at temperatures of 20° to 150° C., preferably 50° to 100° C., in water or organic solvents.

Examples of organic solvents are alcohols, such as methanol, ethanol or the propyl alcohols, or hydrocarbons, such as benzene or toluene, or chlorinated hydrocarbons, such as chlorobenzene or methylene chloride.

c) 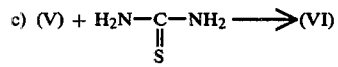

The reaction takes place by melting together the reactants at temperatures of 150° to 220° C., preferably 170° to 190° C. and the starting compound (V) must be in the form of the hydrochloride.

(d)

The reaction takes place at temperatures of 0° to 120° C., preferably 20° to 80° C., in water or organic solvents which are inert towards the reactants.

Examples of inert organic solvents are ethers, such as dioxane or tetrahydrofurane, or hydrocarbons, such as benzene or toluene, or chlorinated hydrocarbons, such as chlorobenzene or chloroform.

(e)

The reaction takes place at temperatures of 60° to 180° C., preferably 80° to 150° C., without a solvent or in the presence of water or alcohols, such as methanol, ethanol or the propyl alcohols, and the starting compound (V) must be in the form of the hydrochloride.

The methods used according to the processes (a) to (e) for the preparation of the compounds of the formula (VI) are known processes which are described in the literature as indicated below:

Process (a): J. Chem. Soc. 1950, 1,515–1,519
Process (b): Org. Syntheses Coll. Vol. IV, 569–570
Process (c): J. prakt. Chemie 75 (1907) 323–327
Process (d): Chem. Ber. 20 (1887) 228–232
Process (e): Ann. 221, (1883) 1–34; Ann. 228, (1885) 243–247

The compounds of the formulae I–IV can be prepared by the following processes:

Process I

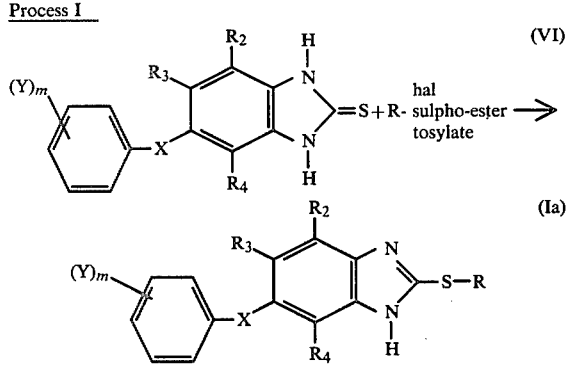

in which R, $R_2$, $R_3$, $R_4$, X, Y and m are as defined under formula I and hal is halogen, sulpho-ester is a monoalkyl sulphate radical and tosylate is a p-toluenesulphonyl radical.

The reaction takes place at temperatures of 0° to 100°, preferably 20° to 80° C., in water, organic solvents or mixtures thereof, in the presence of a base. If organic bases are used, an additional solvent can be dispensed with.

Organic solvents are, for example, alcohols, ethers or ketones. Bases are to be understood as meaning, for example, an alkali or organic bases, such as pyridine or tertiary amines.

The methods used according to Process I for the preparation of the compounds of the formula Ia are known processes which are described in the literature as indicated below:

J. Chem. Soc. 1949, 3,311–3,315
Chem. Abstr. 53 8,124 e (Yakugaka Zasski 78, 1,378–1,382 (1958)
Chem. Abstr. 52 11,773 d (1958)

Process II

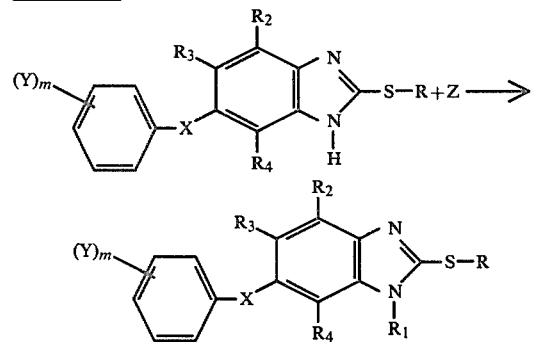

in which formulae R, $R_1$, $R_2$, $R_3$, $R_4$, X, Y and m are as defined under formula I and Z is as defined specifically in process variants (a) to (d) described below.

(a) Z=$(R_1)_2$O or $R_1$-Hal, in which $R_1$ is alkanoyl or benzoyl and Hal is halogen.

The reaction is carried out at temperatures of −20° to +100° C., preferably 0° to 60° C., in inert organic solvents, in the presence of organic or inorganic bases or without bases.

Examples of organic solvents are: ethers, such as dioxane or tetrahydrofurane, hydrocarbons, such as benzene or toluene, and, in addition, dimethylformamide. Bases are to be understood as meaning, for example, pyridine or NaH.

(b) Z=$R_1$Cl or $R_1$-ester, in which $R_1$ is alkylsulphonyl, phenylsulphonyl or methylphenylsulphonyl.

The reaction is carried out at temperatures of −20° to +100° C., preferably 0° to 60° C., in inert organic solvents, in the presence of organic or inorganic bases, or without bases.

Examples of organic solvents are: ethers, such as dioxane or tetrahydrofurane, hydrocarbons, such as benzene or toluene, and, in addition, dimethylformamide.

(c) Z=$R_1$Cl, in which $R_1$ is N,N-dialkylcarbamoyl or N,N-dialkylthiocarbamoyl.

The reaction is carried out at temperatures of 20° to 150° C., preferably 50° to 100° C., in water or organic solvents, in the presence of bases or without bases.

Examples of organic solvents are: ethers, such as dioxane or tetrahydrofurane, and hydrocarbons, such as benzene or toluene. Bases are to be understood as meaning, for example, NaOH, KOH, an alkali metal carbonate, a trialkylamine or pyridine.

(d) Z=$R_1$-Hal, in which $R_1$ is alkoxycarbonyl and Hal is halogen.

The reaction is carried out at temperatures of −20° to +100° C., preferably 0° to 60° C., in inert organic solvents, in the presence of organic or inorganic bases, or without bases.

Examples of organic solvents are: ethers, such as dioxane or tetrahydrofurane, hydrocarbons, such as benzene or toluene, and, in addition, dimethylformamide. Bases are to be understood as meaning, for example, pyridine or NaH.

The methods used in process II for the preparation of the compounds of the formula Ib are known processes which are described in J. Het. Chem. 6 (1969) 23–28.

Process III

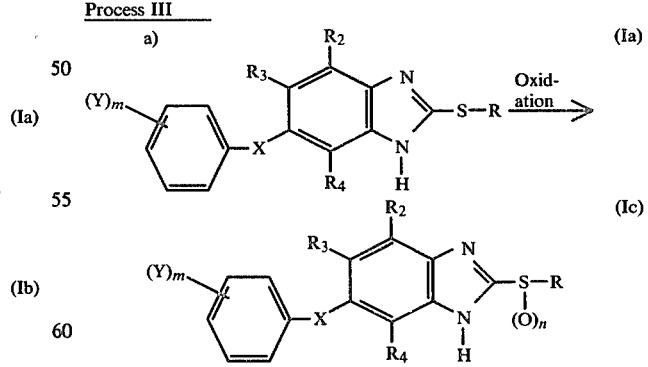

in which formulae R, $R_2$, $R_3$, $R_4$, X, Y and m are as defined under formula I and n is 1 or 2.

The oxidation takes place at temperatures of −20° to +100° C., preferably 0° to 50° C., in water or organic acids in the presence of $KMnO_4$, per-acids, for example peracetic acids or m-chloroperbenzoic acid, or $H_2O_2$, m-chloroperbenzoic acid being a preferred oxidising agent when n is 1, whilst peracetic acid and $H_2O_2$ are particularly suitable for the oxidation when n is 2.

The methods used according to Process III for carrying out the oxidation of the compounds of the formula Ia are known processes which are described in the literature as indicated below: J. Chem. Soc. 1949, 3,311–3,315

Process IV

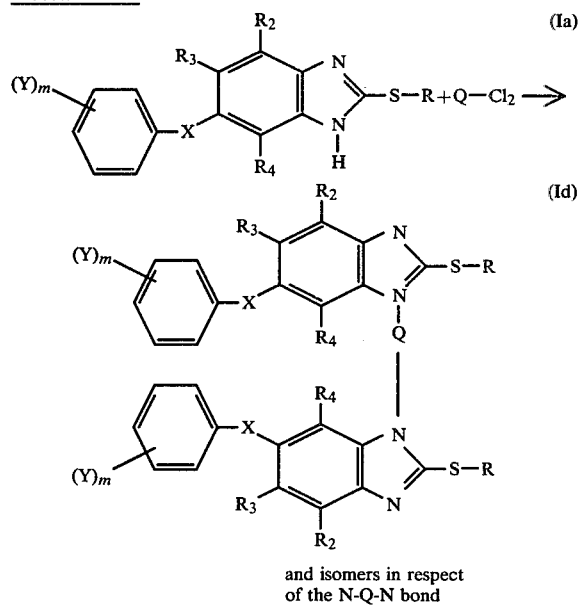

and isomers in respect of the N-Q-N bond in which formulae R, $R_2$, $R_3$, $R_4$, X, Y and m are as defined under formula I and Q is a carbonyl, thiocarbonyl or oxalyl group.

The reaction takes place at temperatures of $-20°$ to $+120°$ C., preferably $-10°$ to $+90°$ C., in organic solvents, in the presence of a base or without a base.

Examples of organic solvents are hydrocarbons, such as benzene, toluene or xylene, or chlorinated hydrocarbons, such as the chlorobenzenes.

Bases are to be understood as meaning organic or inorganic bases, for example pyridine or a trialkylamine and NaOH or $Na_2CO_3$.

The method used according to Process IV is a known process which is described in U.S. Pat. No. 3,256,294.

Some of the starting compounds of the formula V used for the preparation of the compounds, according to the invention, of the formula I are known. Thus, for example, some of the compounds of the formula V are described in Swiss patent specification No. 462,847. These starting compounds can be prepared by known processes. On the other hand, the compounds of the formula VI, which act as intermediates, are to be regarded as novel.

EXAMPLE 1

Preparation of 5-chloro-6-(2′,4′-dichlorophenoxy)-2-methylthio-benzimidazole 73 ml of methyl iodide are added dropwise in the course of 30 minutes to a solution of 400 g of 5-chloro-6-(2′,4′-dichlorophenoxy)-2H-1,3-dihydro-benzimidazole-2-thione and 175 g of potassium hydroxide in a mixture of 175 ml of water and 350 ml of alcohol, the temperature being kept between 10° and 15° C. by cooling. In order to bring the reaction to completion, the reaction mixture is stirred further, first for 30 minutes at room temperature, then for 1 hour at 50° C. and then for a further 18 hours at room temperature.

The resulting emulsion is poured as a thin stream, in the course of 30 minutes, into 5 l of water and a colourless precipitate forms; this is filtered off, washed with 3 l of water and dried in vacuo at 50° C. This gives 400 g of 5-chloro-6-(2′,4′-dichlorophenoxy)-2-methylthio-benzimidazole with a melting point of 178° C., which corresponds to a yield of 98%.

The product purified by recrystallisation from alcohol/water melts at 185°–186° C.

EXAMPLE 2

Preparation of 5-chloro-6-(2′,4′-dichlorophenoxy)-2-methylsulphinyl-benzimidazole A solution of 19.5 g of 90% pure m-chloroperbenzoic acid in 450 ml of chloroform is added dropwise in the course of 30 minutes to a solution, which has been cooled to 0° to 5° C., of 35 g of 5-chloro-6-(2′,4′-dichlorophenoxy)-2-methylthio-benzimidazole in 1,750 ml of chloroform, with stirring. The mixture is stirred for a further 3 hours at 0° to 5° C. and then for 15 hours at room temperature and then is freed from the small amount of precipitate which arises. The filtrate, which still contains residues of m-chloroperbenzoic acid, is treated with sodium bisulphite solution, washed with water, dried over calcium chloride, filtered and concentrated in vacuo. After recrystallising the residue from 500 ml of ethyl acetate, and at the same time clarifying the hot solution with active charcoal, and then drying the white crystals at 50° C., 26 g of 5-chloro-6-(2′,4′-dichlorophenoxy)-2-methylsulphinyl-benzimidazole with a melting point of 206°–208° C. are obtained, which corresponds to a yield of 69%.

EXAMPLE 3

Preparation of 5-chloro-6-(2′,4′-dichlorophenoxy)-2-methylsulphonyl-benzimidazole 122 5 ml of 40% strength peracetic acid are added dropwise in the course of 30 minutes to a solution, which is kept at room temperature by cooling, of 100 g of 5-chloro-6-(2′,4′-dichlorophenoxy)-2-methylthiobenzimidazole in 800 ml of glacial acetic acid, with stirring. The resulting dark red solution is stirred for a further 15 hours at room temperature. A viscous suspension forms and 4 l of demineralised water are added to this. The precipitate formed is then filtered off with suction, washed with water and dried in vacuo at 50° C. This gives 96 g of 5-chloro-6-(2′,4′-dichlorophenoxy)-2-methylsulphonylbenzimidazole with a melting point of 215°–218° C., which corresponds to a yield of 89%.

EXAMPLE 4

Preparation of 5-chloro-6-(2′,4′-dichlorophenoxy)-1(3)-methoxycarbonyl-2-methylthio-benzimidazole 4.5 g of methyl chloroformate are added slowly dropwise to a solution, which has been cooled to 18° C., of 10 g of 5-chloro-6-(2′,4′-dichlorophenoxy)-2-methylthio-benzimidazole in 100 ml of pyridine, with stirring and cooling. The mixture is stirred for a further 15 hours at room temperature and then poured into a mixture of 200 ml of concentrated hydrochloric acid and 350 g of ice and the precipitate is filtered off with suction. The material which has been filtered off with suction is washed with water until neutral, dried at room temperature and mixed to a suspension with 100 ml of absolute ethanol, the suspension is heated to the reflux temperature and then cooled to 5° C., water is added, the mixture is filtered and the product is dried at 50° C. in vacuo. This gives 11.2 g of 5-chloro-6-(2',4'-dichlorophenoxy)-1(3)-methoxycarbonyl-2-methylthio-benzimidazole with a melting point of 62°–66° C., which corresponds to a yield of 96%.

Table 1

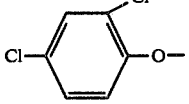

| No. | R₃ | Z | Melting point in °C. |
|-----|-----|---|----------------------|
| 1 | Cl | 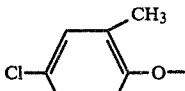 | 185–186 |
| 2 | Cl | 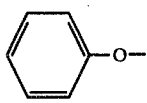 | 158–159 |
| 3 | Cl | 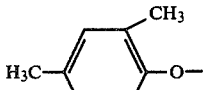 | 179–180 |
| 4 | Cl | 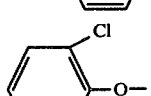 | 169–170 |
| 5 | Cl | 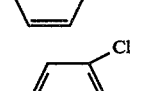 | 172–173 |
| 6 | Cl | 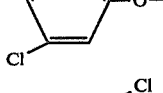 | 127–129 |
| 7 | Cl | 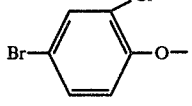 | 196–197 |
| 8 | Cl | 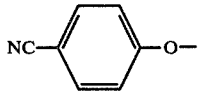 | |
| 9 | Cl | 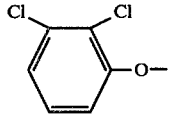 | 175–176 |
| 10 | Cl | | |
| 11 | CH₃ | 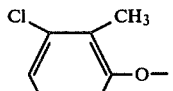 | 191–193 |

Table 1-continued

[Structure: benzimidazole with R3 and X substituents, and 2-S-CH3 group, NH]

| No. | R3 | Z | Melting point in °C. |
|-----|-----|---|---------------------|
| 12 | Cl | 2-methoxyphenoxy (OCH3, O—) | 203–204 |
| 13 | CH3 | 2,5-dichlorophenylthio (Cl, Cl, S—) | 198–199 |
| 14 | Cl | 2,6-dimethylphenoxy (CH3, CH3, O—) | 184–186 |
| 15 | CH3 | 2,4-dichlorophenoxy (Cl, Cl, O—) | 171–173 |
| 16 | Cl | 2,5-dichlorophenylthio (Cl, Cl, S—) | 209–211 |
| 17 | CH3 | 4-chloro-2-methylphenoxy (Cl, CH3, O—) | 184–186 |
| 18 | CH3 | 4-tert-butylphenoxy ((CH3)3C—, O—) | 80–82 |
| 19 | Cl | 4-(sec-butyl)phenoxy (CH3—CH2—CH(CH3)—, O—) | 125–127 |
| 20 | CH3 | 4-chloro-2-methoxyphenoxy (OCH3, Cl, O—) | 95–97 |
| 21 | Cl | phenylthio (S—) | 155–157 |
| 22 | CH3 | phenylthio (S—) | 118–124 |
| 23 | CH3 | 2,3-dichlorophenoxy (Cl, Cl, O—) | 162–164 |
| 24 | CH3 | 2,6-dimethylphenoxy (CH3, CH3, O—) | 226–228 |

Table 1-continued

[Structure: benzimidazole with R₃, X substituents and 2-SCH₃ group]

| No. | R₃ | Z | Melting point in °C. |
|---|---|---|---|
| 25 | Cl | 4-(CH₃S)-C₆H₄-O— | 155–157 |
| 26 | H | 2,4-di-Cl-C₆H₃-O— | 155–156 |
| 27 | H | 2,4,5-tri-Cl-C₆H₂-O— | 211–212 |
| 28 | H | 4-F-C₆H₄-S— | 131–134 |
| 29 | H | 2-Cl-C₆H₄-O— | 152–154 |
| 30 | H | 2,5-di-Cl-C₆H₃-O— | 172–174 |
| 31 | H | 4-Br-2-Cl-C₆H₃-O— | 177–178 |
| 32 | H | 2,3-di-Cl-C₆H₃-O— | 174–175 |
| 33 | H | C₆H₅-S— | 139–141 |
| 34 | H | 4-NC-C₆H₄-O— | 167–168 |
| 35 | H | C₆H₅-O— | 124–126 |
| 36 | H | 4-Cl-C₆H₄-O— | 122–125 |
| 37 | H | 4-CH₃-C₆H₄-O— | 105–108 |

Table 1-continued
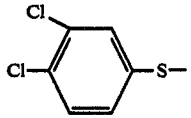
| No. | R₃ | Z | Melting point in °C. |
|---|---|---|---|
| 38 | H | 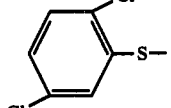 | 157–159 |
| 39 | H | 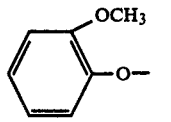 | 190–192 |
| 40 | H | 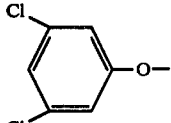 | 145–147 |
| 41 | H | 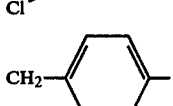 | 191–192 |
| 42 | H | 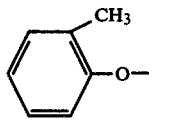 | 118–121 |
| 43 | H | 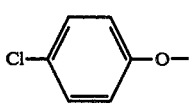 | 137–139 |
| 44 | H | 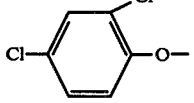 | 192–194 |
| 45 | CH₃O— | 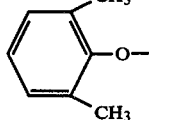 | 165–168 |
| 46 | H | 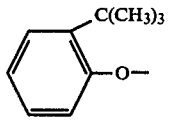 | 163–165 |
| 47 | H | 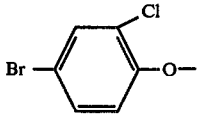 |  |
| 48 | CH₃ | 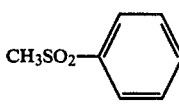 |  |
| 49 | CH₃ | 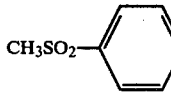 |  |
| 50 | Cl | 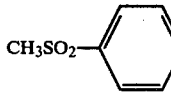 | 210–214 |

Table 1-continued
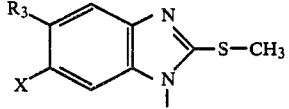
| No. | R₃ | Z | Melting point in °C. |
|---|---|---|---|
| 51 | Cl | 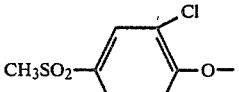 | |
| 52 | Cl | 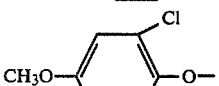 | |
| 53 | Cl |  | |
| 54 | Cl | 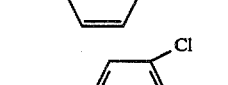 | |
| 55 | Cl | 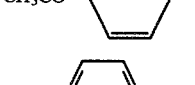 | |
| 56 | Cl | 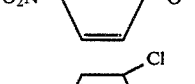 | |
| 57 | H | 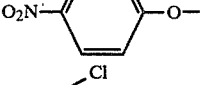 | 169–170 |
| 58 | Br | 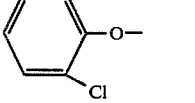 | |
| 59 | CH₃O— | 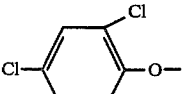 | |
| 60 | CH₃O— | 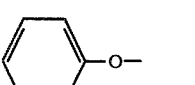 | |
| 61 | C₂H₅O— | 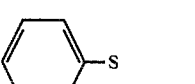 | |
| 62 | C₄H₅O— | 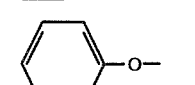 | |

Table 2

| No. | Compound | Melting point in °C. |
|---|---|---|
| 1 | 5-(2,4-dichlorophenoxy)-4-chloro-2-(methylthio)-1H-benzimidazole | 93–95 |
| 2 | 5-(2,4-dichlorophenoxy)-6-chloro-2-(methylthio)-1H-benzimidazole* | 112–115 |

Table 3

(Structure: 5-chloro-6-(2,4-dichlorophenoxy)-2-(methylthio)-1-R₁-benzimidazole)

| No. | R₁ | Melting point in °C. |
|---|---|---|
| 1 | —COOCH₃ * | 62–66 |
| 2 | —COCH₃ * | 121–130 |
| 3 | —COOC₄H₉ * | |

* the structural formula

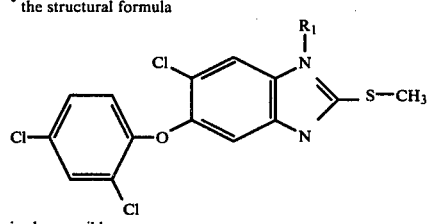

is also possible.

Table 4

(Structure: 5-chloro-6-(2,4-dichlorophenoxy)-2-(S—R)-1H-benzimidazole)

| No. | R | Melting point in °C. |
|---|---|---|
| 1 | —CH₂—CH=CH₂ | 147–150 |
| 2 | —(CH₂)₃CH₃ | 122–125 |
| 3 | —CH₂—C₆H₅ | 63–65 |
| 4 | —CH₂—C≡CH | 136–139 |
| 5 | —C₂H₅ | 65–70 |
| 6 | —CH(CH₃)₂ | 168–171 |
| 7 | —(CH₂)₅CH₃ | 89–92 |
| 8 | —CH₂—(2,6-dichlorophenyl) | 90–95 |
| 9 | —CH₂—(4-nitrophenyl) | |

Table 5

| No. | Compound | Melting point in °C. |
|---|---|---|
| 1 | 5-chloro-6-(2,4-dichlorophenoxy)-2-(methylsulfinyl)-1H-benzimidazole | 204–206 |
| 2 | 5-chloro-6-(2,4-dichlorophenoxy)-2-(methylsulfonyl)-1H-benzimidazole | 215–218 |

Table 5-continued

| No. | Compound | Melting point in °C. |
|-----|----------|----------------------|
| 3 | 5-chloro-6-(2,4-dichlorophenoxy)-2-(ethylsulfinyl)-1H-benzimidazole | 289–294 |
| 4 | 5-chloro-6-(phenylthio)-2-(methylsulfonyl)-1H-benzimidazole | 191–193 |
| 5 | 5-methoxy-6-(2,4-dichlorophenoxy)-2-(methylsulfinyl)-1H-benzimidazole | 166–170 |
| 6 | 4-chloro-5-(2,4-dichlorophenoxy)-2-(methylsulfinyl)-1H-benzimidazole | 197–200 |
| 7 | 4,6-dichloro-5-(2,4-dichlorophenoxy)-2-(methylsulfinyl)-1H-benzimidazole | 239–243 |
| 8 | 5-chloro-6-(2,3-dichlorophenoxy)-2-(methylsulfinyl)-1H-benzimidazole | |
| 9 | 5-chloro-6-(4-bromo-2-chlorophenoxy)-2-(methylsulfinyl)-1H-benzimidazole | |
| 10 | 5-methoxy-6-(2,4-dichlorophenoxy)-2-(methylsulfinyl)-1H-benzimidazole | 166–170 |
| 11 | 5-chloro-6-(4-chloro-2-methylphenoxy)-2-(methylsulfinyl)-1H-benzimidazole | 185–187 |

The anthelmintic activity of the benzimidazole derivatives of the formula I is demonstrated with the aid of the following experiment:

Experiment on rats infested with *Fasciola hepatica*

White laboratory rats were infested with liver flukes (*Fasciola hepatica*). After the end of the pre-patency period, 3 infested rats per experiment were treated with the particular active ingredient, which was administered in the form of a suspension by probang, once per day on three successive days. Each active ingredient was tested in doses of 300, 100, 30 and 10 mg/kg of body weight. Two weeks after administration of the active ingredient, the test animals were killed and dissected.

An evaluation was made after dissection of the test animals, by comparing the number of parasites which had remained in the bile ducts with that in untreated control animals infested in the same way and at the same time.

In therapeutically effective doses, the agent was tolerated by the rats without giving rise to symptoms.

Table 6

Minimal dose of active ingredient for full action against liver flukes

| Compound No. | Dose in mg/kg |
|---|---|
| 1 (T 1) | 3 × 10 |
| 2 (T 1) | 3 × 30 |
| 3 (T 1) | 3 × 100 |
| 4 (T 1) | 3 × 30 |
| 5 (T 1) | 3 × 100 |
| 6 (T 1) | 3 × 30 |
| 7 (T 1) | 3 × 10 |
| 9 (T 1) | 3 × 10 |
| 11 (T 1) | 3 × 100* |
| 14 (T 1) | 3 × 10 |
| 15 (T 1) | 3 × 10 |
| 17 (T 1) | 3 × 300* |
| 23 (T 1) | 3 × 10 |
| 24 (T 1) | 3 × 30* |
| 25 (T 1) | 3 × 100* |
| 26 (T 1) | 3 × 30 |
| 28 (T 1) | 3 × 100* |
| 30 (T 1) | 3 × 30 |
| 31 (T 1) | 3 × 10 |
| 33 (T 1) | 3 × 30 |
| 35 (T 1) | 3 × 30 |
| 36 (T 1) | 3 × 100 |
| 37 (T 1) | 3 × 30 |
| 38 (T 1) | 3 × 30 |
| 39 (T 1) | 3 × 100 |
| 40 (T 1) | 3 × 100 |
| 42 (T 1) | 3 × 100* |
| 43 (T 1) | 3 × 100 |
| 44 (T 1) | 3 × 100 |
| 45 (T 1) | 3 × 100 |
| 1 (T 2) | 3 × 30 |
| 2 (T 2) | 3 × 100 |
| 1 (T 3) | 3 × 10 |
| 2 (T 3) | 3 × 10 |
| 1 (T 4) | 3 × 10 |
| 2 (T 4) | 3 × 30 |
| 3 (T 4) | 3 × 100 |
| 4 (T 4) | 3 × 10 |
| 5 (T 4) | 3 × 10 |
| 7 (T 4) | 3 × 100 |
| 1 (T 5) | 3 × 10 |
| 2 (T 5) | 3 × 30 |
| 3 (T 5) | 3 × 100* |
| 5 (T 5) | 3 × 10 |
| 6 (T 5) | 3 × 100 |
| 7 (T 5) | 3 × 100 |

*not tested at lower dosages

The active ingredients according to the invention are used for combating parasitic helminths in domestic and useful animals, such as cattle, sheep, goats, cats and dogs. They can be administered to the animals either as a single dose or repeatedly, the individual administrations preferably being between 0.5 and 100 mg per kg of body weight, depending on the species of animal. By protracted administration, a better action is achieved in some cases, or it is possible to manage with lower total doses. The active ingredients, or the mixtures containing them, can also be added to the feed or the drinks. The ready-to-use feed contains the substances of the formula I preferably in a concentration of 0.005 to 0.1% by weight. The agents can be administered to the animals in the form of solutions, emulsions, suspensions (drenches), powders, tablets, bolusses or capsules, per-orally or abomasally. Substances used to prepare these administration forms are, for example, conventional solid excipients, such as kaolin, talc, bentonite, sodium chloride, calcium phosphate and cottonseed meal, or liquids which do not react with the active ingredients, such as oils and other solvents and diluents harmless to the animal organism. If the physical and toxicological properties of solutions or emulsions permit, the active ingredients can also be injected into the animals, for example subcutaneously. Furthermore, administration of the active ingredients to the animals by means of salt licks or molasses blocks is also possible.

If the anthelmintic agents are in the form of a feed concentrate, carrier substances used are, for example, hay, production rations, fodder grain or protein concentrates. Such feeds can also contain, in addition to the active ingredients, additives, vitamins, antibiotics, chemotherapeutic agents or other pesticides, mainly bacteriostatic agents, fungistatic agents and coccidiostatic agents or hormone preparations, substances having an anabolic action or other substances which promote growth, influence the quality of the meat of animals for slaughter or are useful to the organism in another way. They can also be combined with other anthelmintics, by which means their action is broadened and suited to given circumstances.

Other anthelmintics are:

Nematocides, for example Alcopar, ascaridole, Banminth II, bephenium, cambendazole, coumaphos, cyanin, diethylcarbamazine, DDVP, 1,4-di-(D-glyconyl)-piperazine, dithiazanine, Dow ET/57, Dowco 132, Gainex, hexachlorophene, hexylresorcinol, Jonit, levamisole, methylene violet, 1-methyl-1-tridecyl-piperazinium-4-carboxylic acid ethyl ester, methyridine, Neguvon, Nematodin, Nemural, Nidanthel, parbendazole, Parvex, phenothiazine, piperazine, polymethylenepiperazine, pyrantel, pyrvinium embonate, Rametin, ronnel, santonin, Shell 1808, stilbazium, tetramisole, thenium, thiabendazole, thymolane, Vermella, mebendazole, oxybendazole, fenbendazole, albendazole and oxfendazole; and Cestocides, for example Acranil, arecoline, Atebrin, bithionol, bithionol-sulphoxide, bunamidine, Cestondin, cambendazole, dibutyl-tin dilaurate, dichlorophene, dioctyl-tin dichloride, dioctyl-tin laurate, filixic acid, hexachlorophene, mepaesin, Nidanthel, praziquantel, Terenol and Yomesan.

The preparation of anthelmintic agents according to the invention is carried out in a manner known per se by intimate mixing and grinding of active ingredients of the general formula I with suitable excipients, if desired with the addition of dispersing agents or solvents which are inert towards the active ingredients.

The active ingredients can be present, and can be employed, in the following processing forms:

Solid processing forms:

granules, coated granules, impregnated granules and homogeneous granules.

Active ingredient concentrates dispersible in water (wettable powders).

Liquid processing forms:

solutions, pastes and emulsions, especially ready-to-use suspensions (drenches).

The particle size of the excipients is advantageously up to about 0.1 mm for dusting agents and wettable powders and 0.01–0.5 mm for granules.

The concentrations of active ingredient are 0.5 to 80% in the solid processing forms and 0.5 to 50% in the liquid processing forms.

Additives which stabilise the active ingredient and/or non-ionic, anionic and cationic substances, which, for example, ensure better wettability (wetting agents) and dispersibility (dispersing agents), can also be added to these mixtures.

EXAMPLE

Powder mixture dispersible in water

25 Parts by weight of an active ingredient of the formula (I) are mixed intensively, in a mixing apparatus, with 7.5 parts by weight of an absorbent excipient, for example silica, and 59.4 parts by weight of an excipient, for example Bolus alba or kaolin, and 0.5 part by weight of oleic acid and 5.3 parts by weight of octylphenol polyglycol ether and 2.3 parts by weight of a stearylbenzimidazole derivative.

This mixture is ground down to a particle size of 5–15 μm in a pin mill or air jet mill. The wettable powder obtained in this way gives a good suspension in water.

What is claimed is:

1. A compound of the formula

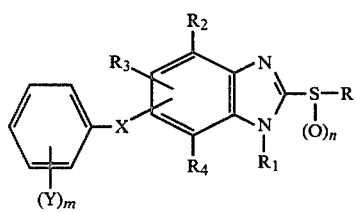

wherein

R is alkyl of from 1 to 6 carbon atoms; alkenyl of from 3 to 5 carbon atoms; alkynyl of from 3 to 5 carbon atoms; benzyl; or benzyl mono- or di-substituted by methyl, halogen or nitro, $R_1$ is hydrogen; alkanoyl of from 1 to 4 carbon atoms; alkoxycarbonyl having 1 to 4 carbon atoms in the alkyl moiety; N,N-dialkylcarbamoyl having 1 to 4 carbon atoms in each alkyl moiety; N,N-dialkylthio carbamoyl having 1 to 4 carbon atoms in each alkyl moiety; alkylsulphonyl of from 1 to 4 carbon atoms; benzoyl; phenylsulphonyl; 4-methylphenylsulphonyl; or the radical

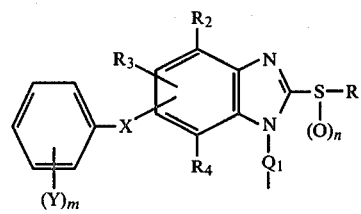

in which

Q is carbonyl, thiocarbonyl or oxalyl, $R_2$ is hydrogen, halogen or methyl, $R_3$ is hydrogen, halogen, methyl or alkoxy of from 1 to 4 carbon atoms, $R_4$ is hydrogen, halogen or methyl, X is oxygen or sulphur, Y is halogen, alkyl of from 1 to 4 carbon atoms, alkoxy of from 1 to 4 carbon atoms, methylthio, methylsulphionyl, methylsulphonyl, trifluoromethyl, nitro, hydroxyl, cyano, or alkanoyl of from 1 to 4 carbon atoms;

m is 0, 1, 2 or 3; and n is 0, 1 or 2.

2. A compound according to claim 1, wherein $R_1$ is hydrogen, alkanoyl of from 1 to 4 carbon atoms, alkoxycarbonyl having 1 to 4 carbon atoms in the alkyl moiety, or benzoyl, $R_2$ is hydrogen, chlorine or methyl, $R_3$ is hydrogen, chlorine, methyl or methoxy, $R_4$ is hydrogen, chlorine or methyl, and Y is halogen, methyl, methoxy, methylthio, methylsulphinyl, methylsulphonyl, acetyl, hydroxy, nitro or cyano.

3. A compound according to claim 2, wherein $R_1$ is hydrogen.

4. A compound according to claim 3, wherein

R is alkyl of from 1 to 6 carbon atoms, $R_2$ is hydrogen, $R_3$ is hydrogen, chlorine or methyl, $R_4$ is hydrogen, X is oxygen, Y is hydrogen or methyl, with the requirement that the 2-position be occupied and the 6-position be unoccupied, m is 1 or 2, and n is 0.

5. A compound according to claim 4 which is 5-chloro-6-(2',4'-dichlorophenoxy)-2-methylthiobenzimidazole.

6. The compound according to claim 4 which is 5-chloro-6-(2'-chloro-4'-bromophenoxy)-2-methylthiobenzimidazole.

7. The compound according to claim 4 which is 5-chloro-6-(2',3'-dichlorophenoxy)-2-methylthiobenzimidazole.

8. The compound according to claim 4 which is 5-chloro-6-(2',3'-dimethylphenoxy)-2-methylthiobenzimidazole.

9. The compound according to claim 4 which is 5-methyl-6-(2',3'-dichlorophenoxy)-2-methylthiobenzimidazole.

10. The compound according to claim 4 which is 6-(2',3'-dichlorophenoxy)-2-methylthiobenzimidazole.

11. A composition for combatting parasitic helminths which comprises (1) an anthelmintically effective amount of a compound according to claim 1 and (2) a suitable excipient or diluent.

12. A method for combatting parasitic helminths in animals which comprises administering to an animal infested with said helminths an anthelmintically effective amount of a compound according to claim 1.

13. A method according to claim 12 in which the helminths are trematodes.

14. A method according to claim 13 in which the helminths are *Fasciola hepatica*.

15. A method for combatting parasitic helminths in animals which comprises administering to an animal infested with said helminths an anthelmintically effective amount of a compound according to claim 2.

16. A method for combatting parasitic helminths in animals which comprises administering to an animal infested with said helminths an anthelmintically effective amount of a compound according to claim 3.

17. A method for combatting parasitic helminths in animals which comprises administering to an animal infested with said helminths an anthelmintically effective amount of a compound according to claim 4.

18. The method according to claim 17 in which the compound is 5-chloro-6-(2',4'-dichlorophenoxy)-2-methylthiobenzimidazole.

19. The method according to claim 17 in which the compound is 5-chloro-6-(2'-chloro-4'-bromophenoxy)-2-methylthiobenzimidazole.

20. The method according to claim 17 in which the compound is 5-chloro-6-(2',3'-dichlorophenoxy)-2-methylthiobenzimidazole.

21. The method according to claim 17 in which the compound is 5-chloro-6-(2',3'-dimethylphenoxy)-2-methylthiobenzimidazole.

22. The method according to claim 17 in which the compound is 5-methyl-6-(2',3'-dichlorophenoxy)-2-methylthiobenzimidazole.

23. The method according to claim 17 in which the compound is 6-(2',3'-dichlorophenoxy)-2-methylthiobenzimidazole.

* * * * *